United States Patent [19]

Hirai et al.

[11] Patent Number: 4,499,180
[45] Date of Patent: Feb. 12, 1985

[54] HEAT-DEVELOPABLE COLOR PHOTOGRAPHIC MATERIALS WITH BASE PRECURSOR

[75] Inventors: Hiroyuki Hirai; Ken Kawata, both of Kanagawa, Japan

[73] Assignee: Fuji Photo Film Co., Ltd., Kanagawa, Japan

[21] Appl. No.: 583,913

[22] Filed: Feb. 27, 1984

[30] Foreign Application Priority Data

Feb. 25, 1983 [JP]  Japan ................................. 58-31614

[51] Int. Cl.³ .......................... G03C 5/54; G03C 1/40; G03C 1/06
[52] U.S. Cl. .................................... 430/559; 430/203; 430/351; 430/353; 430/617; 430/619; 430/955
[58] Field of Search ............... 430/203, 351, 353, 617, 430/619, 955, 559

[56] References Cited

U.S. PATENT DOCUMENTS 3,220,846 11/1965 Tinker et al. ..................... 430/617
4,088,496 5/1978 Merkel ............................... 430/353
4,463,079 7/1984 Naito et al. ........................ 430/203

*Primary Examiner*—Richard L. Schilling

*Attorney, Agent, or Firm*—Sughrue, Mion, Zinn, Macpeak & Seas

[57] ABSTRACT

A heat-developable color photographic material is disclosed. The material is comprised of a support base, a binder, a light-sensitive silver halide, a dye releasing redox compound which reduces the light-sensitive silver halide and releases a hydrophilic dye by reacting with the light-sensitive silver halide by heating; and a base precursor. The base precursor is represented by the general formula:

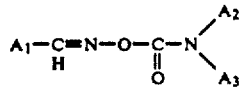

wherein the substituents are defined within the specification. The material is capable of forming dye images with high density by heating the material after exposure in a substantially water free state. The images can be obtained in a short period of time and maintain their color density during storage. Further, the material produces a relatively low degree of fog based on the high degree of image density obtained.

4 Claims, No Drawings

HEAT-DEVELOPABLE COLOR PHOTOGRAPHIC MATERIALS WITH BASE PRECURSOR

FIELD OF THE INVENTION

The present invention relates to novel photographic material containing a dye releasing redox compound which releases a hydrophilic dye by reacting with light-sensitive silver halide when heated in a substantially water free state.

The present invention also relates to heat-developable color light-sensitive materials, i.e., heat-developable color photographic materials, containing a base precursor.

The term "base precursor" herein used means a substance which releases a basic component by thermal decomposition.

BACKGROUND OF THE INVENTION

A photographic process using silver halide has been widely used hitherto, because it is excellent in photographic characteristics such as sensitivity or control of gradation, etc., as compared with other photographic process such as electrophotography or diazophotography. In recent years, techniques capable of rapidly and easily obtaining image have been developed by modifying the image formation processing of light-sensitive materials (photographic materials) using silver halide by replacing the prior wet processing which uses a developing solution, etc., with a dry processing which uses heating, etc.

Heat-developable photographic materials are known in the field of this art. Heat-developable photographic materials and processes thereof have been described in, for example, *Shashinkogaku no Kiso*, published by Corona Co., pages 553–555 (1979), *Eizojoho*, page 40 (Apr. 1979), *Nebletts Handbook of Photography and Reprography*, 7th Ed. (Van Nostrand Reinhold Company), page 32, U.S. Pat. Nos. 3,152,904, 3,301,678, 3,392,020 and 3,457,075, British Pat. Nos. 1,131,108 and 1,167,777 and *Research Disclosure*, pages 9–15, RD-17029(June 1978).

There are many known dry processes for obtaining color images. With respect to a process for forming color images by coupling an oxidation product of a developing agent with a coupler, p-phenylenediamine reducing agents and phenolic or active methylene couplers have been proposed in U.S. Pat. No. 3,531,286, p-aminophenol reducing agents have been proposed in U.S. Pat. No. 3,761,270, sulfonamidophenol reducing agents have been proposed in Belgian Pat. No. 802,519 and *Research Disclosure*, pages 31 and 32 (Sept. 1975), and combinations of sulfonamidophenol reducing agents and 4-equivalent couplers have been proposed in U.S. Pat. No. 4,021,240.

However, in these processes, the color images become impure, because reduced silver images and color images are formed at the same time on exposed parts after thermal development. Attempts at eliminating this problem include a process which comprises removing silver images by liquid treatment and a process which comprises transferring only dyes to another layer, for example, a sheet having a receiving layer. However, with these processes it is not easy to distinguish the dyes from unreacted substances and transfer only the dyes.

Further, a process which comprises forming a silver salt using a dye into which a nitrogen containing heterocyclic group is introduced and releasing the dye by thermal development has been described in *Research Disclosure*, pages 54–58, RD-16966 (May 1978). However, this process is not generally used because it is difficult to control the release of dyes in areas which were not exposed to light and, consequently, clear-cut images cannot be obtained.

With respect to a process for forming positive color images by a heat-sensitive silver-dye bleaching process, useful dyes and a method of bleaching have been described in, for example, *Research Disclosure*, pages 30 to 32, RD-14433 (April 1976), and pages 14–15, RD-15227 (December 1976), and U.S. Pat. No. 4,235,957, etc.

In this process, however, it is necessary to use extra steps and materials, for example, heating is carried out by superposing a sheet containing an activating agent in order to promote bleaching of the dyes. Further, the resulting color images are gradually reduced and bleached by coexistent free silver during preservation for a long period of time.

Further, a process for forming color images using leuco dyes has been described in, for example, U.S. Pat. Nos. 3,985,565 and 4,022,617. However, with this process the photographic materials gradually color during preservation, because the leuco dyes are difficult to contain in the photographic materials.

SUMMARY OF THE INVENTION

The present invention provides novel color light-sensitive materials which form dye images by heating in a substantially water free state.

An object of the present invention is to provide light-sensitive materials capable of obtaining color images having a high density in a short period of time.

Another object of the present invention is to provide light-sensitive materials containing a novel base precursor capable of obtaining color images having a high density and a low degree of fog.

A further object of the present invention is to provide heat-developable color light-sensitive materials having excellent stability over the passage of time. The term "stable over the passage of time" means that changes of photographic properties such as maximum density, minimum density or sensitivity, etc., are small during preservation of photographic materials before thermal development.

Such objects have been attained by providing heat-developable color photographic materials which comprise a support base and at least a light-sensitive silver halide, a binder, a dye releasing redox compound which reduces the light-sensitive silver halide and releases a hydrophilic dye by reacting with the light-sensitive silver halide by heating, and a base precursor represented by the following general formula (I), provided on the support base.

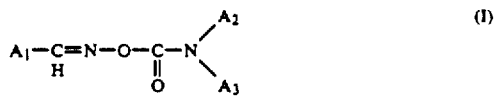

wherein $A_1$ represents a substituent selected from an alkyl group, a substituted alkyl group, a cycloalkyl group, an alkenyl group, an aralkyl group, an aryl group, a substituted aryl group, an acyl group and a heterocyclic group, preferably an aryl group and a substituted aryl group, $A_2$ and $A_3$ represent each a substituent selected from a hydrogen atom, an alkyl group, a substituted alkyl group, a cycloalkyl group and an aralkyl group, preferably an alkyl group and a substituted alkyl group, more preferably an alkyl group having carbon atoms of 6 or less, and $A_2$ and $A_3$ may form a ring by linking together or

may form an imino group by a double bond.

DETAILED DESCRIPTION OF THE INVENTION

Examples of alkyl groups in $A_1$ to $A_3$ include straight chain or branched chain alkyl groups having 1 to 18 carbon atoms. Examples of substituents in the substituted alkyl groups include a hydroxyl group, an alkoxy group, a cyano group, a carboxyl group, a carboalkoxy group, a carbamoyl group and a halogen atom, etc.

Examples of cycloalkyl groups in $A_1$ to $A_3$ include 5- or 6-member cycloalkyl groups having 5 to 10 carbon atoms. Examples of alkenyl groups include an allyl group, a crotyl group and a cinnamyl group, etc.

Examples of aralkyl groups include a benzyl group, a β-phenethyl group and a benzhydryl group, etc. Examples of aryl groups include a phenyl group, a naphthyl group and an anthryl group, etc. Examples of substituents in the substituted aryl groups include an alkyl group, an alkoxy group, a dialkylamino group, a cyano group, a nitro group, a hydroxyl group and a halogen atom, etc. Examples of heterocyclic groups include a pyridyl group, a furyl group, a thienyl group, a pyrrole group and an indolyl group, etc. Examples of acyl groups include acyl groups having 2 to 18 carbon atoms derived from aliphatic or aromatic carboxylic acids.

Examples of $A_2$ and $A_3$ which form a ring by linking together include

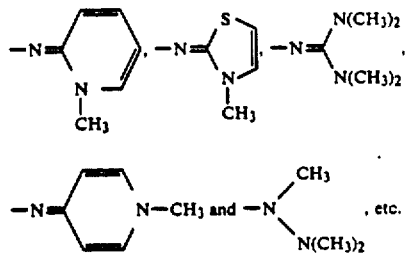

Further, examples of

which represents an imino group include

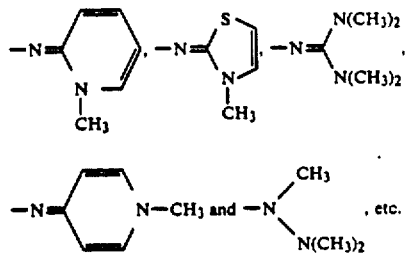

In the following, preferred examples of compounds covered by the general formula (I) are shown.

n-C₃H₇CH=N—OCON(CH₃)₂

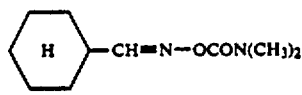

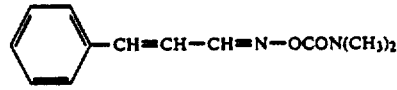

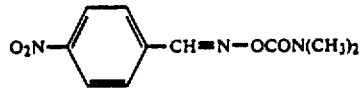

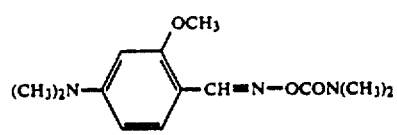

n-C₇H₁₅CH=N—OCON(CH₃)₂

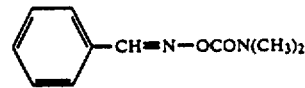

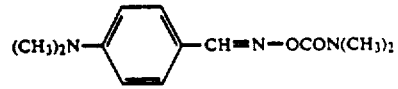

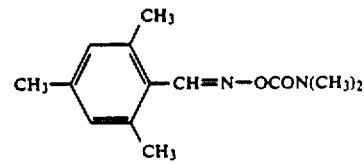

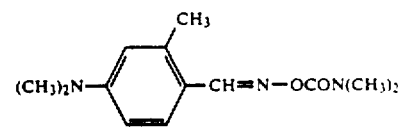

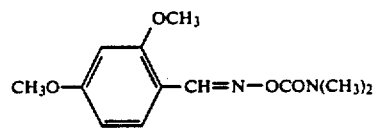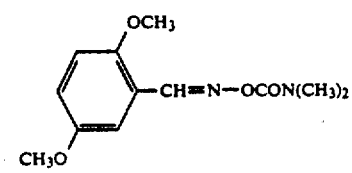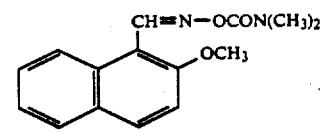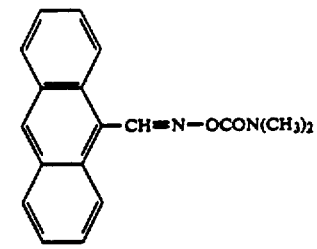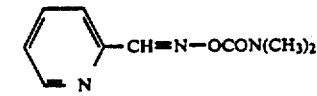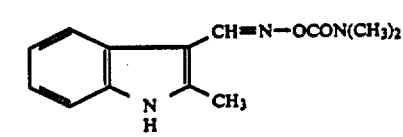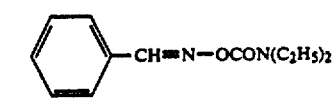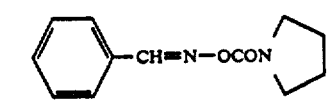
-continued
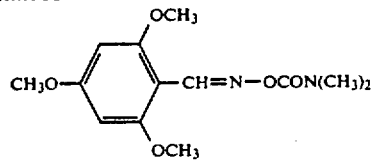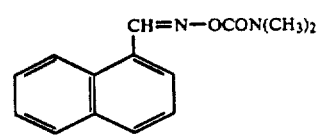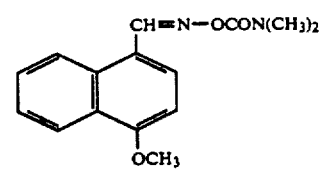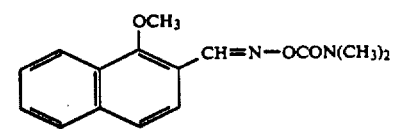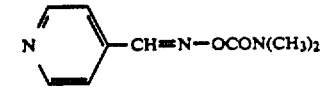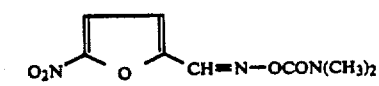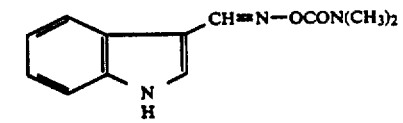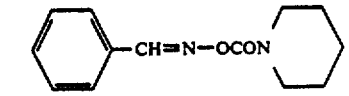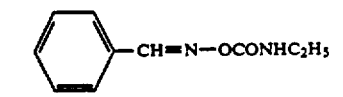

-continued

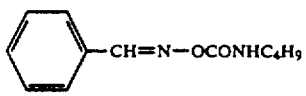 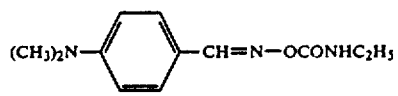

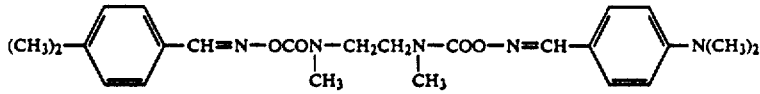

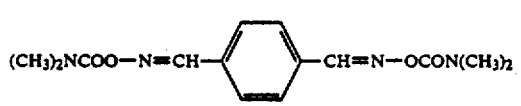 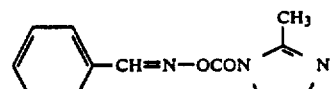

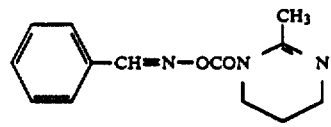 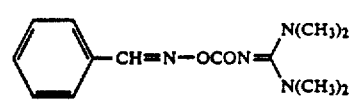

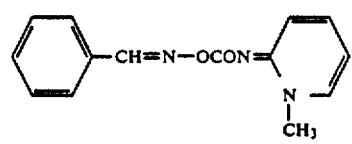 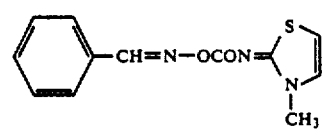

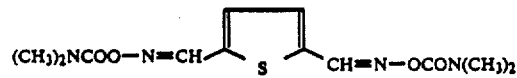 

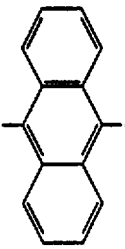

In the following, processes for synthesizing base precursors of the present invention are described.

The base precursors of the present invention can be easily synthesized by a reaction (A) of carbamoyl chloride derivatives with aldoximes or a reaction (B) of isocyanates with aldoximes.

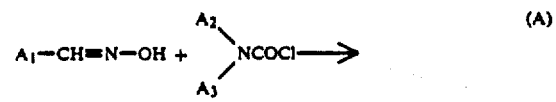

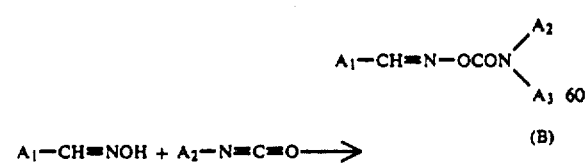

The carbamoyl chloride derivatives of the raw materials are easily obtained from corresponding amine and phosgene by a process described in literatures (refer to J. Chem. Soc., 307 (1947), etc.). The aldoxime derivatives are easily obtained from corresponding aldehyde and hydroxylamine by a process described in literatures (refer to Org. Synth., II 313 (1943), etc.). The desired products can be obtained in a high yield by carrying out the condensation reaction of carbamoyl chloride with aldoxime in an aprotic solvent such as acetonitrile, ether or hydrofuran, etc., at 20° to 50° C. In the following, examples of synthesis are described.

SYNTHESIS EXAMPLE 1

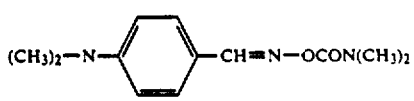

4.8 g of oily sodium hydride (50%) was added to a suspension containing 16.4 g of p-N,N-dimethylbenzaldoxime in acetonitrile. After being stirred for 1 hour, 11.1 ml of N,N-dimethylcarbamoyl chloride was added slowly, and the mixture was stirred for another 4 hours.

The resulting precipitate was filtered off, sufficiently washed and dried. Yield: 22 g. m.p.: 148° to 149° C.

Other carbamate derivatives were synthesized by the same process as described above. Examples of them are shown in the following table.

TABLE

| $A_1$ | $A_2$ | $A_3$ | Melting Point (°C.) |
|---|---|---|---|
| (CH$_3$)$_2$N—⌬— | C$_2$H$_5$— | C$_2$H$_5$— | 81–82 |
| O$_2$N—⌬— | CH$_3$— | CH$_3$— | 145–146 |
| O$_2$N—⌬— | C$_2$H$_5$— | C$_2$H$_5$— | 126–129 |
| ⌬N— | CH$_3$— | CH$_3$— | 73–75 |
| ⌬— | —(CH$_2$)$_5$— ($A_2$ and $A_3$ form a ring) | | 136 |

SYNTHESIS EXAMPLE 2

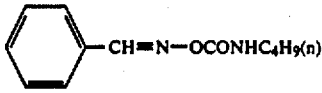

⌬—CH=N—OCONHC$_4$H$_9$(n)

5 g of butyl isocyanate was added to 6.0 g of benzaldoxime. After refluxing for 2 hours with heating, ether was removed by evaporation. Yield: 4g, Oil (20° C.)

SYNTHESIS EXAMPLE 3

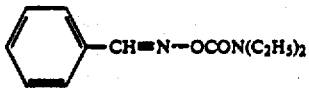

⌬—CH=N—OCON(C$_2$H$_5$)$_2$

To a solution containing 12.1 g of benzaldoxime in acetonitrile, 16 g of N,N-diethylcarbamoyl chloride was added and 8 ml of triethylamine was slowly added. After the reaction mixture was refluxed for 2 hours with heating, it was poured into iced water. The product was extracted with ethyl acetate, dried and purified by column chromatography. Yield: 17 g, Oil (20° C.)

Other carbamate derivatives were synthesized by the same process as described above.

Some examples of them are shown in the following table.

TABLE

| $A_1$ | $A_2$ | $A_3$ | Melting Point (°C.) |
|---|---|---|---|
| ⌬— | C$_3$H$_7$— | C$_3$H$_7$— | Oily |
| OCH$_3$/CH$_3$O—⌬— | C$_2$H$_5$— | C$_2$H$_5$— | 48–50 |
| OCH$_3$/CH$_3$O—⌬— | CH$_3$— | CH$_3$— | 95–97 |
| (CH$_3$)$_2$N—⌬— | C$_2$H$_5$— | C$_2$H$_5$— | Oily |

The base precursors of the present invention can be used in an amount over a wide range. It is preferred to use them in an amount of 50% by weight or less based on the total weight of the coating layer. More preferably, a range of 0.01% by weight to 40% by weight is suitable.

The base precursors of the present invention may be used alone or as a mixture of two or more of them. Further, they may be used together with known base precursors as a combination. Examples of known base precursors have been described in British Pat. No. 998,949, U.S. Pat. No. 3,220,846 and Japanese Patent Publication (unexamined) No. 22625/75, etc.

According to the heat-developable color photographic materials of the present invention, it is possible to form silver images and movable dyes in the parts corresponding to the silver images at the same time by only heating after imagewise exposing to light.

In this specification, the term "thermal development" means that heating is carried out in a substantially water free state to release a dye by an oxidation-reduction reaction between exposed silver halide and the dye releasing redox compound.

Namely, when the heat-developable color photographic materials of the present invention are imagewise exposed to light and developed with heating in a substantially water free state, an oxidation-reduction reaction between light-sensitive silver halide and the reducing dye releasing compound is caused by a catalytic function the exposed silver halide to form a silver image on the exposed part. In this step, the dye releasing redox compound is oxidized by light-sensitive silver halide to become an oxidized product and, consequently, a hydrophilic movable dye is released. Thus, in the exposed part, a silver image and a movable dye are obtained. In this case, when a base is present, the above-described reaction is accelerated. When the movable dye is moved to, for example, a dye fixing layer, a dye image is obtained. However, if the base is directly contained in the photographic material, stability to the passage of time is inferior. When the base precursors of the present invention are used, stability to the passage of time of the photographic materials can be improved, because the base is released only when developing at a high temperature by heating.

In the above case, negative type emulsions are used. However, when using auto-positive type emulsions, the same result as when using negative type emulsions is obtained, except that silver images and movable dyes are obtained in the nonexposed parts.

It is a feature of the present invention that the oxidation-reduction reaction between light-sensitive silver halide and the dye releasing redox compound, and the subsequent dye releasing reaction are caused at a high temperature in a dry state which does not substantially contain water. In this case, the term "high temperature" means a temperature of 80° C. or more, and the term "dry state which does not substantially contain water" means a state which is in equilibrium with water in the air but water is not fed from the outside of the system. Such a state has been described in *The Theory of the Photographic Process*, edited by T. H. James, Macmillan, 4th Ed., page 374. The fact that sufficient reactivity is shown in even the dry state which does not substantially contain water can be confirmed from the fact that the reactivity of the sample which is dried in vacuum of $10^{-3}$ Hg for 1 day is not reduced.

Hitherto, the dye releasing reaction is believed to be caused by an attack of the so-called nucleophilic reagent and it is generally carried out in a liquid having a high pH of 10 or more. Accordingly, it is an unexpected fact that high reactivity is shown at a high temperature in the dry state which does not substantially contain water like the present invention. Further, the dye releasing redox compounds of the present invention are capable of causing an oxidation-reduction reaction with silver halide without using the so-called auxiliary developing agent. This is an unexpected result from the prior knowledge obtained by wet development at near ordinary temperature.

The above-described reaction proceeds particularly well to show a high image density, when an organic silver salt oxidizing agent is present. Accordingly, it is a particularly preferred embodiment to use the organic silver salt oxidizing agent in combination.

The dye releasing redox compound which releases a hydrophilic dye used in the present invention is a compound described in European Patent Publication (unexamined) No. 76,492 as a dye releasing compound and is represented by the following general formula:

$R_d$—SO$_2$—D wherein $R_d$ represents a reducing group capable of being oxidized by the silver halide; and D represents an image forming dye portion containing a hydrophilic group.

The above-described compound is oxidized correspondingly to or reversely corresponding to latent image distributed imagewise in the silver halide and releases imagewise a mobile dye.

The detail definitions of $R_d$ and D, examples of the specific compounds and synthesis examples thereof are described in European Patent Publication (unexamined) No. 76,492.

As the dye releasing redox compounds used in the present invention, the compounds as described, for example, in U.S. Pat. No. 4,055,428, Japanese Patent Publication (unexamined) Nos. 12642/81, 16130/81, 16131/81, 650/82 and 4043/82, U.S. Pat. Nos. 3,928,312 and 4,076,529, U.S. Published Patent Application Ser. No. B 351,673, U.S. Pat. Nos. 4,135,929 and 4,198,235, Japanese Patent Publication (unexamined) No. 46730/78, U.S. Pat. Nos. 4,273,855, 4,149,892, 4,142,891 and 4,258,120, etc., are also effective in addition to the above-described compounds.

Further, the dye releasing redox compounds which release a yellow dye as described, for example, in U.S. Pat. Nos. 4,013,633, 4,156,609, 4,148,641, 4,165,987, 4,148,643, 4,183,755, 4,246,414, 4,268,625 an 4,245,028, Japanese Patent Publication (unexamined) Nos. 71072/81, 25737/81, 138744/80, 134849/80, 106727/77, 114930/76, etc., can be effectively used in the present invention.

The dye releasing redox compounds which release a magenta dye as described, for example, in U.S. Pat. Nos. 3,954,476, 3,932,380, 3,931,144, 3,932,381, 4,268,624 and 4,255,509, Japanese Patent Publication (unexamined) Nos. 73057/81, 71060/81, 134850/80, 40402/80, 36804/80, 23628/78, 106727/77, 33142/80 and 53329/80, etc., can be effectively used in the present invention.

The dye releasing redox compounds which release a cyan dye as described, for example, in U.S. Pat. Nos. 3,929,760, 4,013,635, 3,942,987, 4,273,708, 4,148,642, 4,183,754, 4,147,544, 4,165,238, 4,246,414 and 4,268,625, Japanese Patent Publication (unexamined) Nos. 71061/81, 47823/78, 8827/77 and 143323/78, etc., can be effectively used in the present invention.

Two or more of the dye releasing redox compounds can be used together. In these cases, two or more dye releasing redox compounds may be used together in order to represent the same color or in order to represent black color.

The dye releasing redox compounds are suitably used in a range from 10 mg/m$^2$ to 15 g/m$^2$ and preferably in a range from 20 mg/m$^2$ to 10 mg/m$^2$ in a total.

The dye releasing redox compound used in the present invention can be introduced into a layer of the photographic material by known methods such as a method as decribed in U.S. Pat No. 2,322,027. In this case, an organic solvent having a high boiling point or an organic solvent having a low boiling point as described below can be used. For example, the dye releasing redox compound is dispersed in a hydrophilic colloid after dissolved in an organic solvent having a high boiling point, for example, a phthalic acid alkyl ester (for example, dibutyl phthalate, dioctyl phthalate, etc.), a phosphoric acid ester (for example, diphenyl phosphate, triphenyl phosphate, tricresyl phosphate, dioctylbutyl phosphate, etc.), a citric acid ester (for example, tributyl acetylcitrate, etc.), a benzoic acid ester (for example, octyl benzoate, etc.), an alkylamide (for example, diethyl laurylamide, etc.), an aliphatic acid ester (for example, dibutoxyethyl succinate, dioctyl azelate, etc.), a trimesic acid ester (for example, tributyl trimesate, etc.), etc., or an organic solvent having a boiling point of about 30° C. to 160° C., for example, a lower alkyl acetate such as ethyl acetate, butyl acetate, etc., ethyl propionate, secondary butyl alcohol, methyl isobutyl ketone, β-ethoxyethyl acetate, methyl cellosolve acetate, cyclohexanone, etc. The above-described organic solvents having a high boiling point and organic solvents having a low boiling point may be used as a mixture thereof.

Further, it is possible to use a dispersion method using a polymer as described in Japanese Patent Publication No. 39853/76 and Japanese Patent Publication (unexamined) No. 59943/76. Moreover, various surface active agents can be used when the dye releasing redox compound is dispersed in a hydrophilic colloid. For this purpose, the surface active agents illustrated in other part of the specification can be used.

In the present invention, if necessary, a reducing agent may be used. The reducing agent is this case is the so-called auxiliary developing agent, which is oxidized by the silver halide and/or the organic silver salt oxidizing agent to form its oxidized product having an ability to oxidize the reducing group $R_a$ in the dye releasing redox compound.

Examples of useful auxiliary developing agents include the compounds specifically described in European Patent Publication (unexamined) No. 76,492.

The silver halide used in the present invention includes silver chloride, silver chlorobromide, silver chloroiodide, silver bromide, silver iodobromide, silver chloroiodobromide and silver iodide, etc.

In the embodiment of the present invention in which the organic silver salt oxidizing agent is not used together with but the silver halide is used alone, particularly preferred silver halide is silver halide partially containing a silver iodide crystal in its grain. That is, the silver halide which shows the X-ray diffraction pattern of pure silver iodide is particularly preferred.

In photographic materials a silver halide containing two or more kinds of halogen atoms can be used. Such silver halide is present in the form of a completely mixed crystal in a conventional silver halide emulsion. For example, the grain of silver iodobromide shows X-ray diffraction pattern at a position corresponding to the mixed ratio of silver iodide crystal and silver bromide crystal but not at a position corresponding to pure silver iodide crystal and pure silver bromide crystal separately.

Particularly preferred examples of silver halide used in the present invention include silver chloroiodide, silver iodobromide, and silver chloroiodobromide each containing silver iodide crystal in its grain and showing X-ray diffraction pattern of silver iodide crystal.

The process for preparing those silver halides is explained taking the case of silver iodobromide. That is, the silver iodobromide is prepared by first adding silver nitrate solution to potassium bromide solution to form silver bromide particles and then adding potassium iodide to the mixture.

Two or more kinds of silver halides in which a particle size and/or a halogen composition are different from each other may be used in mixture.

An average particle size of the silver halide used in the present invention is preferably from 0.001 μm to 10 μm and more preferably from 0.001 μm to 5 μm.

The silver halide used in the present invention may be used as is. However, it may be chemically sensitized with a chemical sensitizing agent such as compounds of sulfur, selenium or tellurium, etc., or compounds of gold, platinum, rhodium or iridium, etc., a reducing agent such as tin halide, etc., or a combination thereof. The details thereof are described in T. H. James, *The Theory of the Photographic Process*, the Fourth Edition, Chapter 5, pages 149 to 169.

In the particularly preferred embodiment of the present invention, an organic silver salt oxidizing agent is used together. The organic silver salt oxidizing agent is a silver salt which forms a silver image by reacting with the above-described image forming substance or a reducing agent coexisting, if necessary, with the image forming substance, when it is heated to a temperature of above 80° C. and, preferably, above 100° C. in the presence of exposed silver halide. By coexisting with the organic silver salt oxidizing agent, the light-sensitive material which provides higher color density can be obtained.

The silver halide used in this case is not always necessary to have the characteristic in that the silver halide contains pure silver iodide crystal in the case of using the silver halide alone. Any silver halide which is known in the art can be used.

Examples of such organic silver salt oxidizing agents include those described in European Patent Publication (unexamined) No. 76,492.

A silver salt of an organic compound having a carboxy group can be used. Typical examples thereof include a silver salt of an aliphatic carboxylic acid and a silver salt of an aromatic carboxylic acid.

In addition, a silver salt of a compound containing a mercapto group or a thione group and a derivative thereof can be used.

Further, a silver salt of a compound containing an imino group can be used. Examples of these compounds include a silver salt of benzotriazole and a derivative thereof as described in Japanese Patent Publication Nos. 30270/69 and 18416/70, for example, a silver salt benzotriazole, a silver salt of alkyl substituted benzotriazole such as a silver salt of methylbenzotriazole, etc., a silver salt of a halogen substituted benzotriazole such as a silver salt of 5-chlorobenzotriazole, etc., a silver salt of carboimidobenzotriazole such as a silver salt of butylcarboimidobenzotriazole, etc., a silver salt of 1,2,4-triazole or 1-H-tetrazole as described in U.S. Pat. No. 4,220,709, a silver salt of carbazole, a silver salt of saccharin, a silver salt of imidazole and an imidazole derivative, and the like.

Moreover, a silver salt as described in *Research Disclosure*, Vol. 170, No. 17029 (June, 1978) and an organic metal salt such as copper stearate, etc., are the organic metal salt oxidizing agent capable of being used in the present invention.

Methods of preparing these silver halide and organic silver salt oxidizing agents and manners of blending them are described in *Research Disclosure*, No. 17029, Japanese Patent Publication (unexamined) Nos. 32928/75, 42529/76, 13224/74 and 17216/75, and U.S. Pat. No. 3,700,458.

A suitable coating amount of the light-sensitive silver halide and the organic silver salt oxidizing agent employed in the present invention is in a total of from 50 mg/m² to 10 g/m² calculated as an amount of silver.

The light-sensitive silver halide and the organic silver salt oxidizing agent used in the present invention are prepared in the binder as described below. Further, the dye releasing redox compound is dispersed in the binder described below.

The binder which can be used in the present invention can be employed individually or in a combination thereof. A hydrophilic binder can be used as the binder according to the present invention. The typical hydrophilic binder is a transparent or translucent hydrophilic colloid, examples of which include a natural substance, for example, protein such as gelatin, a gelatin derivative, etc., a cellulose derivative, a polysaccharide such as starch, gum arabic, etc., and a synthetic polymer, for example, a water-soluble polyvinyl compound such as polyvinyl alcohol, polyvinyl pyrrolidone, acrylamide polymer, etc. Another example of the synthetic polymer compound is a dispersed vinyl compound in a latex form which is used for the purpose of increasing dimensional stability of a photographic material.

The silver halide used in the present invention can be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, can be contained in these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei may also be substituted.

As nuclei having a ketomethylene structure, 5- or 6-membered heterocyclic nuclei such as a pyrazolin-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc., may also be used in merocyanine dyes and complex merocyanine dyes.

These sensitizing dyes can be employed individually, and can also be employed in combination thereof. A combination of sensitizing dyes is often used, particularly for the purpose of supersensitization. Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, Japanese Patent Publication (unexamined) Nos. 110618/77 and 109925/77, etc.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, etc., can be present. The combinations described in U.S. Pat. Nos. 3,615,613, 3,615,641, 3,617,295 and 3,635,721 are particularly useful.

A support used in the photographic material or used as the dye fixing material, if desired, according to the present invention is that which can endure at the processing temperature. As an ordinary support, not only glass, paper, metal or analogues thereto may be used, but also an acetyl cellulose film, a cellulose ester film, a polyvinyl acetal film, a polystyrene film, a polycarbonate film, a polyethylene terephthalate film, and a film related thereto or a plastic material may be used. Further, a paper support laminated with a polymer such as polyethylene, etc., can be used. The polyesters described in U.S. Pat. Nos. 3,634,089 and 3,725,070 are preferably used.

In the present invention, various kinds of dye releasing activators can be used. The dye releasing activator means a substance which accelerates the oxidation-reduction reaction between the light-sensitive silver halide and/or the organic silver salt oxidizing agent and dye releasing redox compound, or accelerates release of a dye by means of its nucleophilic action to the oxidized dye releasing redox compound in the dye releasing reaction subsequently occurred, and a base and a base precursor can be used. It is particularly advantageous to use these dye releasing activators in order to accelerate the reactions in the present invention.

Examples of preferred bases are amines which include trialkylamines, hydroxylamines, aliphatic polyamines, N-alkyl substituted aromatic amines, N-hydroxyalkyl substituted aromatic amines and bis[p-(dialkylamino)phenyl]methanes. Further, betaine tetramethylammonium iodide and diaminobutane dihydrochloride as described in U.S. Pat. No. 2,410,644, and urea and organcic compounds including amino acids such as 6-aminocaproic acid as described in U.S. Pat. No. 3,506,444 are useful. As stated at the beginning, the base precursor is a substance which releases a basic component by heating, and the known base precursors are used together with novel base precursors of the present invention as a combination. Typical examples of such base precursors used together with the novel base precursor of the present invention are described in British Pat. No. 998,949. A preferred base precursor is a salt of a carboxylic acid and an organic base, and examples of the suitable carboxylic acids inclucde trichloroacetic acid and trifluoroacetic acids and examples of the suitable bases include guanidine, piperidine, morphololine, p-toluidine and 2-picoline, etc. Guanidine trichloroacetate as described in U.S. Pat. No. 3,220,846 is particularly preferred. Further, aldonic amides as described in Japanese Patent Publication (unexamined) No. 22625/75 are preferably used because they decompose at a high temperature to form bases.

These dye releasing activators can be used in an amount of a broad range. A useful range is up to 50% by weight based on the amount of a dry layer coated of the photographic material. A range of 0.01% by weight to 40% by weight is more preferred.

It is advantageous to use a compound represented by the general formula described below in the heat-developable color photographic material in order to accelerate development and accelerate release of a dye.

(A)

wherein $A_1$, $A_2$, $A_3$ and $A_4$, which may be the same or different, each represents a hydrogen atom or a substituent selected from an alkyl group, a substituted alkyl group, a cycloalkyl group, an aralkyl group, and aryl group, a substituted aryl group and a hetrocyclic group; and $A_1$ and $A_2$ or $A_3$ and $A_4$ may combine with each other to form a ring.

The above-described compound can be used in an amount of broad range. A useful range is up to 20% by weight based on the amount of a dry layer coated of the photographic material. A range of 0.1% by weight to 15% by weight is more preferred.

It is advantageous to use a water releasing compound in the present invention in order to accelerate the dye releasing reaction.

The water releasing compound means a compound which releases water by decomposition during heat development. These compounds are particularly known in the field of printing of fabrics, and $NH_4Fe(SO_4)_2.12\text{-}H_2O$, etc., as described in Japanese Patent Publication (unexamined) No. 88386/75 are useful.

Further, in the present invention, it is possible to use a compound which activates development and stabilizes the image at the same time. Particularly, it is preferred to use isothiuroniums including 2-hydroxyethylisothiuronium trichloroacetate as described in U.S. Pat. No. 3,301,678, bisisothiuroniums including 1,8-(3,6-dioxaoctane)bis(isothiuronium trifluoroacetate), etc., as described in U.S. Pat. No. 3,669,670, thiol compounds as described in German Patent Application (OLS) No. 2,162,714, thiazolium compounds such as 2-amino-2-thiazolium trichloroacetate, 2-amino-5-bromoethyl-2-thiazolium trichloroacetate, etc., as described in U.S. Pat. No. 4,012,260, compounds having α-sulfonylacetate as an acid part such as bis(2-amino-2-thiazolium)-methylene-bis(sufonylacetate), 2-amino-2-thiazolium phenylsulfonylacetate, etc., as described in U.S. Pat. No. 4,060,420, and compounds having 2-carboxycarboxamide as an acid part as described in U.S. Pat. No. 4,088,496.

In the present invention, it is possible to use a thermal solvent. The term "thermal solvent" means a non-hydrolyzable organic material which melts at a temperature of heat treatment and melts at a lower temperature of heat treatment when it is present together with other components. Preferred examples of thermal solvents include compounds which can act as a solvent for the developing agent and compounds having a high dielectric constant which accelerate physical development of silver salts. Examples of preferred thermal solvents include those described in European Patent Publication (unexamined) No. 76,492.

In the present invention, though it is not always necessary to further incorporate substances or dyes for preventing irradiation or halation in the photographic material, because the photographic material is colored by the dye releasing redox compound, it is possible to add filter dyes or light absorbing materials, etc., into the photographic material as described in Japanese Patent Publication No. 3692/73 and U.S. Pat. Nos. 3,253,921, 2,527,583 and 2,956,879, etc., in order to further improve sharpness. It is preferred that these dyes have a thermal bleaching property. For example, dyes as described in U.S. Pat. Nos. 3,769,019, 3,745,009 and 3,615,432 are preferred.

The photographic material used in the present invention may contain, if necessary, various additives known for the heat-developable photographic materials and may have a layer other than the light-sensitive layer, for example, an antistatic layer, an electrically conductive layer, a protective layer, an intermediate layer, an antihalation layer, a strippable layer, etc.

The photographic emulsion layer and other hydrophilic colloid layers in the photographic material of the present invention may contain various surface active agents for various purposes, for example, as coating aids or for prevention of electrically charging, improvement of lubricating property, emulsification, prevention of adhesion, improvement of photographic properties (for example, acceleration of development, rendering hard tone or sensitization), etc.

For example, it is possible to use nonionic surface active agents such as saponin (steriod saponin), alkylene oxide derivatives (for example, polyethylene glycol, polyethylene glycol/polypropylene glycol condensates, polyethylene glycol alkyl ethers or polyethylene glycol alkylaryl ethers, polyethylene glycol esters, polyethylene glycol sorbitan esters, polyalkylene glycol alkylamines or amides, polyethylene oxide adducts of silicone, etc.), glycidol derivatives (for example, alkenylsuccinic acid polyglycerides, alkylphenol polyglycerides, etc.), polyhydric alcohol aliphatic acid esters or saccharide alkyl esters, etc.; anionic surface active agents containing acid groups such as a carboxy group, a sulfo group, a phospho group, a sulfate group, a phosphate group, etc., such as alkylcarboxylic acid salts, alkylsufonate, alkylbenzenesulfonate, alkylnaphthalenesulfonate, alkyl sulfuric acid esters, alkylphosphoric acid ester, N-acyl-N-alkyltaurines, sulfosuccinic acid esters, sulfoalkyl polyoxyethylene alkylphenyl ethers, polyoxyethylene alkylphosphoric acid esters, etc.; ampholytic surface active agents such as amino acids; aminoalkylsulfonic acids, aminoalkylsulfuric acid esters or phosphoric acid esters, alkylbetaines, amine oxides, etc.; and cationic surface active agents such alkylamine salts, aliphatic or aromatic quaternary ammonium salts, heterocyclic quaternary ammonium salts such as pyridinium salts, imidazolium salts, etc., aliphatic or heterocyclic phosphonium salts, aliphatic or heterocyclic sulfonium salts, etc.

Of the above-described surface active agents, polyethylene glycol type nonionic surface active agents having a recurring unit of ethylene oxide in their molecules may be preferably incorporated into the photographic material. It is particularly preferred that the molecule contains 5 or more of the recurring units of ethylene oxide. The nonionic surface active agents capable of satisfying the above-described conditions are well known as to their structures, properties and methods of synthesis. These nonionic surface active agents are widely used even outside this field. Representative references relating to these agents include: *Surfactant Science Series*, Vol. 1, Nonionic Surfactants (edited by Martin J. Schick, Marcel Dekker Inc., 1967), and *Surface Active Ethylene Oxide Adducts* (edited by Schoufeldt N. Pergamon Press, 1969). Amoung the nonionic surface active agents described in the above-mentioned references, those capable of satisfying the above-described conditions are preferably employed in connection with the present invention.

The nonionic surface active agents can be used individually or as a mixture of two or more of them.

The polyethylene glycol type nonionic surface active agents can be used in an amount of less than 100% by weight, preferably less than 50% by weight, based on a hydrophilic binder.

The photographic material of the present invention may contain a cationic compound containing a pyridinium salt. Examples of the cationic compounds containing a pyridinium group used are described in PSA Journal Section B 36 (1953), U.S. Pat. Nos. 2,648,604 and 3,617,247, Japanese Patent Publication Nos. 30074/69 and 9503/69 etc.

In the photographic material and the dye fixing material of the present invention, the photographic emulsion layer and other binder layers may contain inorganic or organic hardeners. It is possible to use chromium salts (chromium alum, chromium acetate, etc.), aldehydes (formaldehyde, glyoxal, glutaraldehyde, etc.), N-methylol compounds (dimethylolurea, methylol dimethylhydantoin, etc.), dioxane derivatives (2,3-dihydroxydioxane, etc.), active vinyl compounds (1,3,5-triacryloylhexahydro-s-triazine, 1,3-vinylsulfonyl-2-propanol, etc.), active halogen compounds (2,4-dichloro-6-hydroxy-s-triazine, etc.), mucohalogenic acids (mucochloric acid, mucophenoxychloric acid, etc.), etc., which are used individually or as a combination thereof.

Examples of various additives include those described in *Research Disclosure*, Vol. 170, No. 17029 (June, 1978), for example, plasticizers, dyes for improving sharpness, antihalation dyes, sensitizing dyes, matting agents, fluorescent whitening agents and fading preventing agents, etc.

If necessary, two or more layers may be coated at the same time by the method described in U.S. Pat. No. 2,761,791 and British Pat. No. 837,095.

Various means for exposure can be used in the present invention. Latent images are obtained by image-wise exposure by radiant rays including visible rays. Generally, light sources used in this invention include tungsten lamps, mercury lamps, halogen lamps such as iodine lamps, xenon lamps, laser light sources, CRT light sources, fluorescent tubes and light-emitting diodes etc.

In the present invention, after the heat-developable color photographic material is exposed to light, the resulting latent image can be developed by heating the whole material to a suitably elevated temperature, for example, about 80° C. to about 250° C. for about 0.5 second to about 300 seconds. A higher temperature or lower temperature can be utilized to prolong or shorten the heating time, if it is within the above-described temperature range. Particularly, a temperature range of about 110° C. to about 160° C. is useful.

As the heating means, a simple heat plate, iron, heat roller, heat generator utilizing carbon or titanium white, etc., or analogues thereto may be used.

In the present invention, a specific method for forming a color image by heat development comprises transfer of a hydrophilic mobile dye. For this purpose, the heat-developable color photographic material of the present invention is composed of a support having thereon a light-sensitive layer (I) containing at least silver halide, if necessary, an organic silver salt oxidizing agent, a dye releasing redox compound which is also a reducing agent for the organic silver salt oxidizing agent and a binder, and a dye fixing layer (II) capable of receiving the hydrophilic dye formed in the light-sensitive layer (I).

The above-described light-sensitive layer (I) and the dye fixing layer (II) may be formed on the same support, or they may be formed on different supports, respectively. The dye fixing layer (II) can be stripped off the light-sensitive layer (I). For example, after the heat-developable color photographic material is exposed imagewise to light, it is developed by heating uniformly and thereafter the dye fixing layer (II) or the light-sensitive layer (I) is peeled apart. Also, when a photographic material having the light-sensitive layer coated on a support and a fixing material having the dye fixing layer (II) coated on a support are separately formed, after the photographic material is exposed imagewise to light and uniformly heated, the mobile dye can be transferred on the dye fixing layer (II) by superposing the fixing material on the light-sensitive layer.

Further, there is a method wherein only the light-sensitive layer (I) is exposed imagewise to light and heated uniformly by superposing the dye fixing layer (II) on the light-sensitive layer (I).

The dye fixing layer (II) can contain, for example, a dye mordant in order to fix the dye. In the present invention, various mordants can be used, and polymer mordants are particularly preferred. In addition to the mordants, the dye fixing layer may contain the bases, base precursor and thermal solvents. In particular, it is particularly preferred to incorporate the bases or base precursor into the dye fixing layer (II) in the cases wherein the light-sensitive layer (I) and the dye fixing layer are formed on different supports.

Preferred polymer mordants used in the present invention can be polymers containing secondary and tertiary amino groups, polymers containing nitrogen-containing heterocyclic moieties, polymers having quaternary cation groups thereof, having a molecular weight of from 5,000 to 200,000, and particularly from 10,000 to 50,000.

For example, there are illustrated vinylpyridine polymers and vinylpyridinium cation polymers as disclosed in U.S. Pat. Nos. 2,548,564, 2,484,430, 3,148,016 and 3,756,814, etc., polymer mordants capable of cross-linking with gelatin as disclosed in U.S. Pat. No. 3,625,694, 3,859,096 and 4,128,538, British Pat. No. 1,277,435, etc., aqueous sol type mordants as disclosed in U.S. Pat. Nos. 3,958,995, 2,721,852 and 2,798,063, Japanese Patent Publication (unexamined) Nos. 115228/79, 145529/79 and 126027/79, etc., water-insoluble mordants as disclosed in U.S. Pat. No. 3,898,088, etc., reactive mordants capable of forming covalent bonds with dyes used as disclosed in U.S. Pat. No. 4,168,976 (Japanese Patent Publication (unexamined) No. 137333/79), etc., and mordants disclosed in U.S. Pat. Nos. 3,709,690, 3,788,855, 3,642,482, 3,488,706, 3,557,066, 3,271,147 and 3,271,148, Japanese Patent Publication (unexamined) Nos. 71332/75, 30328/78, 155528/77, 125/78 and 1024/78, etc.

In addition, mordants disclosed in U.S. Pat. Nos. 2,675,316 and 2,882,156 can be used.

The dye fixing layer (II) can have a white reflective layer. For example, a layer of titanium dioxide dispersed in gelatin can be provided on the mordant layer on a transparent support. The layer of titanium dioxide forms a white opaque layer, by which reflection color images of the transferred color images which can be observed through the transparent support is obtained.

Typical dye fixing material used in the present invention is obtained by mixing the polymer containing ammonium salt groups with gelatin and applying the mixture to a transparent support.

The transfer of dyes from the light-sensitive layer to the dye fixing layer can be carried out using a dye transfer assistant. Examples of useful dye transfer assistant include water and an alkaline aqueous solution containing sodium hydroxide, potassium hydroxide and an inorganic alkali metal salt. Further, a solvent having a low boiling point such as methanol, N,N-dimethylformamide, acetone, diisobutyl ketone, etc., and a mixture of such a solvent having a low boiling point with water or an alkaline aqueous solution can be used. The dye transfer assistant can be employed by wetting the image receiving layer with the transfer assistant or by incorporating it in the form of water of crystallization or microcapsules into the material.

The present invention will now be described in greater detail by reference to the following examples and comparative examples which are given here for illustrative purposes only and are by no means intended to limit the scope of the invention.

EXAMPLE 1

40 g of gelatin and 26 g of KBr were dissolved in 3,000 ml of water. The resulting solution was stirred while maintaining the temperature at 50° C.

A solution prepared by dissolving 34 g of silver nitrate in 200 ml of water was then added to the above-described solution over 10 minutes.

Thereafter, a solution prepared by dissolving 3.3 of g KI in 100 ml of water was added over 2 minutes.

The pH of the resulting silver iodobromide emulsion was controlled to cause precipitation, and excess salts were removed.

Thereafter, the pH was adjusted to 6.0 to obtain 400 g of silver iodobromide emulsion.

In the following, a process for producing a dispersion of the dye releasing redox compound in gelatin is illustrated.

5 g of the following releasing redox compound

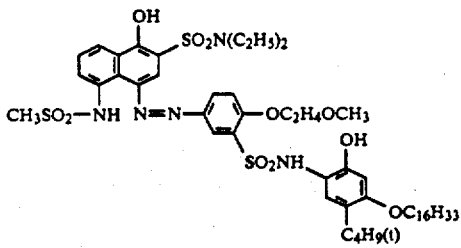

0.5 g of sodium succinic acid-2-ethylhexyl ester sulfonate and 5 g of tricresyl phosphate (TCP) were weighed and dissolved in 30 ml of ethyl acetate by heating to about 60° C. After the resulting solution was blended with 100 g of a 10% solution of gelatin with stirring, the mixture was dispersed by a homogenizer at 10,000 rpm for 10 minutes. The resulting dispersion is referred to as a dispersion of a dye releasing redox compound.

In the following, a process for preparing a photographic coating material is illustrated.

| (a) | Light-sensitive silver iodobromide emulsion | 25 g |
| (b) | Dispersion of dye releasing redox compound | 33 g |
| (c) | 5% Aqueous solution of the following compound: | 10 ml |

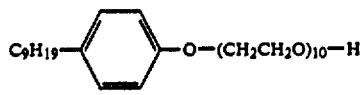

| (d) | 10% aqueous solution of the following compound: H$_2$NSO$_2$N(CH$_3$)$_2$ | 4 ml |
| (e) | Solution prepared by dissolving 2.5 g of the following base precursor of the present invention in 20 ml of ethanol: | |

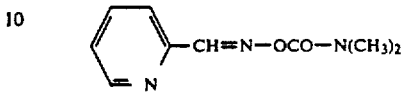

The above-described (a) to (e) were blended. After dissolved with heating, the mixture was applied to a polyethylene terephthalate film having a thickness of 180μ so as to result in a wet film thickness of 30μm. After the coated sample was dried, it was imagewise exposed to light at 2,000 luxes for 10 seconds using a tungsten lamp. Thereafter, it was uniformly heated for 60 seconds on a heat block heated to 140° C. This sample was called Sample A.

Then, Sample B produced by adding 4 ml of water instead of the compound of the present invention (e), and was subjected to the same procedure as that described above.

In the following, a process for producing an image receiving material having an image receiving layer was illustrated.

10 g of poly(methyl acrylate-co-N,N,N-trimethyl-N-vinylbenzylammonium chloride) (ratio of methyl acrylate to vinylbenzylammonium chloride was 1:1) was dissolved in 200 ml of water, and the resulting solution was blended with 100 g of 10% lime-treated gelatin. The resulting mixture was applied to a paper base laminated with polyethylene containing dispersed titanium dioxide so as to result in a wet film thickness of 90μm. After the sample was dried, it was used as an image receiving material.

After the image receiving material was dipped in water, it was superposed on the above-described heated photographic material A or B so as to come in contact with the film face.

After they were heated for 6 seconds on a heat block at 80° C., the image receiving material was separated from the photographic material, by which a negative magenta image was obtained on the image receiving material. When the density of this negative image was measured by means of a Macbeth reflection densitometer (RD-519), the following results were obtained.

| Sample No. | Maximum Density | Minimum Density |
| --- | --- | --- |
| A (The Present Invention) | 2.05 | 0.20 |
| B (Comparison) | 0.03 | 0.03 |

It is understood from the above results that the base precursor of the present invention provides images of high density.

When Sample A was subjected to the same processing as described above after being preserved at 60° C. for 2 days, the minimum density and the maximum density were 0.26 and 2.07, respectively. These results show that the sample of the present invention has good preservation stability.

EXAMPLE 2

The same procedure as in Example 1 was carrried out except that the following base precursors were used, and the following results were obtained.

TABLE

| Sample No. | Base Precursor | | Maximum Density |
|---|---|---|---|
| C | (CH₃)₂N—⌬—CH=N—OCON(C₂H₅)₂ | 2.7 g | 2.02 |
| D | ⌬—CH=N—OCON(piperidine) | 3.0 g | 1.98 |
| E | (CH₃)₂N—⌬—CH=N—OCON(C₃H₇—n)₂ | 3.5 g | 1.85 |
| F | ⌬—CH=N—OCON(morpholine) | 3.0 g | 1.45 |
| G | CH₃—CH=CH—CH=NOCON(CH₃)₂ | 2.5 g | 1.63 |
| H | ⟨H⟩—CH=N—OCON(C₂H₅)₂ | 3.5 g | 1.80 |
| I | ⌬—CH=N—OCO—N(CH₃-substituted piperidine) | 3.0 g | 2.00 |
| J | n-C₇H₁₅—CH=N—OCON(CH₃)₂ | 2.5 g | 1.72 |

It is understood from the above-described results that the base precursors of the present invention provide excellent results with respect to maximum image density.

EXAMPLE 3

Dispersions of dye releasing redox compounds were produced by the same procedure as in Example 1 except that the following dye releasing redox compounds were used instead of the dye releasing redox compound used in Example 1.

Dispersion (I): 5 g of the following dye releasing redox compound was used.

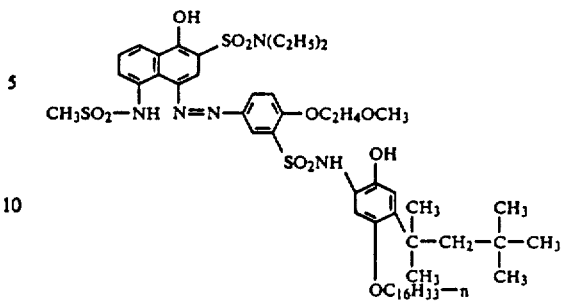

Dispersion (II): 7.5 g of the following dye releasing redox compound was used.

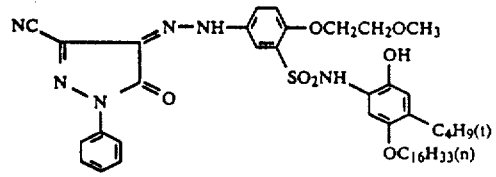

Dispersion (III): 5 g of the following dye releasing redox compound was used.

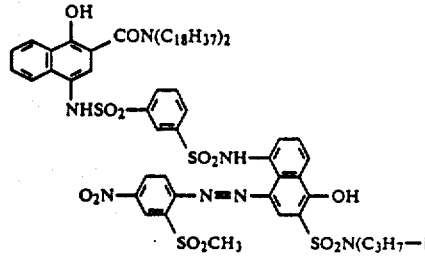

Samples were produced by the same procedure as in Example 1, and they were processed similarly. Results obtained are shown in the following.

| Dispersion of Dye Releasing Redox Compound | Compound of the Present Invention | Maximum Density | Minimum Density |
|---|---|---|---|
| Dispersion (I) (magenta) | Presence | 2.24 | 0.17 |
| | Absence | 0.03 | 0.03 |
| Dispersion (II) (yellow) | Presence | 1.82 | 0.20 |
| | Absence | 0.03 | 0.03 |
| Dispersion (III) (cyan) | Presence | 2.28 | 0.42 |
| | Absence | 0.20 | 0.05 |

It is understood from the above-described results that the base precursors of the present invention provide images with a high maximum density.

EXAMPLE 4

In the following, an example of using an organic silver salt oxidizing agent is illustrated. Process for preparing a silver benzotriazole emulsion:

28 g of gelatin and 13.2 g of benzotriazole were dissolved in 3,000 ml of water. The resulting solution was stirred while maintaining the temperature at 40° C. To the solution, a solution prepared by dissolving 17 g of silver nitrate in 100 ml of water was added over 2 minutes.

The pH of the resulting silver benzotriazole emulsion was controlled to cause precipitation, and excess salts were removed. Thereafter, the pH was adjusted to 6.0 to obtain 400 g of a silver benzotriazole emulsion.

Using the resulting silver benzotriazole emulsion, the following photographic coating material was prepared.

| (a) | Silver iodobromide emulsion (which was described in Example 1) | 20 g |
|---|---|---|
| (b) | Silver benzotriazole emulsion | 10 g |
| (c) | Dispersion of dye releasing redox compound | 33 g |
| (d) | 5% Aqueous solution of the following compound: <br> $C_9H_{19}$—⟨phenyl⟩—O—$(CH_2CH_2O)_{10}$—H | 10 ml |
| (e) | 10% Aqueous solution of the following compound: <br> $H_2NSO_2N(CH_3)_2$ | 4 ml |
| (f) | Solution prepared by dissolving 3 g of the following base precursor of the present invention in 20 ml of ethanol: <br> 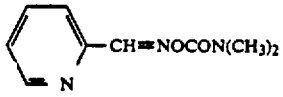 | |

The above described (a) to (f) were blended. The mixture was then processed by the same procedure as in Example 1. Results obtained are shown in the following.

| Sample | Maximum Density | Minimum Density |
|---|---|---|
| Containing 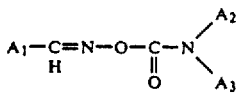-CH=NOCON(CH$_3$)$_2$ | 2.20 | 0.20 |
| Absence of the base precursor | 0.03 | 0.03 |

It is understood that the base precursor of the present invention provides an image having high density.

While the invention has been described in detail and with reference to specific embodiments thereof, it will be apparent to one skilled in the art that various changes and modifications can be made therein without departing from the spirit and scope thereof.

What is claimed is:

1. A heat-developable color photographic material, comprising:
   a support base having thereon:
   a binder having dispersed therein;
   a light-sensitive silver halide;
   a dye releasing redox compound which reduces the light-sensitive silver halide and releases a hydrophilic dye by reacting with the light-sensitive silver halide by heating; and
   a base precursor represented by the following general formula:

$$A_1-\underset{H}{C}=N-O-\underset{\underset{O}{\|}}{C}-N\overset{A_2}{\underset{A_3}{\diagup}}$$

wherein $A_1$ represents a substituent selected from an alkyl group, a substituted alkyl group, a cycloalkyl group, an alkenyl group, and aralkyl group, an aryl group, a substitued aryl group, an acyl group and a heterocyclic group, $A_2$ and $A_3$ represent each a substituent selected from a hydrogen atom, an alkyl group, a substituted alkyl group, a cycloalkyl group, and an aralkyl group, and $A_2$ and $A_3$ may form a ring by linking together or $$-N\overset{A_2}{\underset{A_3}{\diagup}}$$

may form an imino group by a double bond.

2. A heat-developable color photographic material as claimed in claim 1, wherein $A_1$ represents an aryl group or a substituted aryl group.

3. A heat-developable color photographic material as claimed in claim 1, wherein $A_2$ and $A_3$ represent an alkyl group or a substituted alkyl group.

4. A heat-developable color photographic material as claimed in claim 1, wherein the base precursor is present in the layer in an amount of 50% by weight or less based on the total weight of the layer.

* * * * *